(12) United States Patent
Howell et al.

(10) Patent No.: US 11,764,831 B2
(45) Date of Patent: *Sep. 19, 2023

(54) WIRELESS BED POWER

(71) Applicant: Hill-Rom Services, Inc., Batesville, IN (US)

(72) Inventors: Charles A. Howell, Batesville, IN (US); William G. Pittenger, Aurora, IN (US); Michael S. Hood, Batesville, IN (US); Edward J. Koors, Indianapolis, IN (US); Steven A. Dixon, Cincinnati, OH (US); Richard J. Schuman, Cary, NC (US); Matthew D. Morgan, Cary, NC (US); Laurie Lee Gutzwiller, Batesville, IN (US); Kelly F. Walton, Cary, NC (US)

(73) Assignee: Hill-Rom Services, Inc., Batesville, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/182,281

(22) Filed: Feb. 23, 2021

(65) Prior Publication Data

US 2021/0184729 A1 Jun. 17, 2021

Related U.S. Application Data

(63) Continuation of application No. 16/122,013, filed on Sep. 5, 2018, now Pat. No. 10,938,446, which is a
(Continued)

(51) Int. Cl.
*H04B 5/00* (2006.01)
*H02J 50/10* (2016.01)
(Continued)

(52) U.S. Cl.
CPC .......... *H04B 5/0037* (2013.01); *H02J 7/0042* (2013.01); *H02J 50/10* (2016.02);
(Continued)

(58) Field of Classification Search
CPC ........ H04B 5/0037; H02J 50/40; H02J 50/10; H02J 50/90; H02J 7/025; A61G 7/018;
(Continued)

(56) References Cited

U.S. PATENT DOCUMENTS

| 5,335,651 A | 8/1994 | Foster et al. |
| 5,729,587 A | 3/1998 | Betz |

(Continued)

FOREIGN PATENT DOCUMENTS

| CA | 2848095 C | 6/2015 |
| JP | 2011160888 A | 8/2011 |

(Continued)

OTHER PUBLICATIONS

PCT Search Report and Written Opinion for PCT/US2014/021507, completed Sep. 8, 2014.

*Primary Examiner* — Cassandra F Cox
(74) *Attorney, Agent, or Firm* — Barnes & Thornburg LLP

(57) ABSTRACT

Patient care equipment includes a wireless coupler that transfers power and/or data between an architectural unit and the patient care equipment. The patient care equipment may also include additional wireless couplers that transfer power and/or data between first and second components of the equipment. The second component may be movable relative to the first component. A structure or hot swapping batteries is also disclosed, the swapped battery being charged on an inductive charging mat.

18 Claims, 14 Drawing Sheets

Related U.S. Application Data continuation of application No. 14/771,929, filed as application No. PCT/US2014/021507 on Mar. 7, 2014, now Pat. No. 10,075,214.

(60) Provisional application No. 61/776,169, filed on Mar. 11, 2013.

(51) Int. Cl.
  *H02J 50/90* (2016.01)
  *H02J 50/40* (2016.01)
  *H02J 7/00* (2006.01)
  *A61G 7/018* (2006.01)
  *A61G 12/00* (2006.01)

(52) U.S. Cl.
  CPC ............ *H02J 50/402* (2020.01); *H02J 50/90* (2016.02); *A61B 2560/0204* (2013.01); *A61B 2560/0214* (2013.01); *A61G 7/018* (2013.01); *A61G 12/005* (2013.01); *A61G 2203/22* (2013.01); *A61G 2203/30* (2013.01)

(58) Field of Classification Search
  CPC .............. A61G 12/005; A61G 2203/22; A61G 2203/30; A61B 2560/0204; A61B 2560/0214
  See application file for complete search history.

(56) References Cited

U.S. PATENT DOCUMENTS

| | | | |
|---|---|---|---|
| 7,075,220 B2 | 7/2006 | Ito et al. | |
| 7,129,970 B2 | 10/2006 | James et al. | |
| 7,158,860 B2 | 1/2007 | Wang et al. | |
| 7,161,322 B2 | 1/2007 | Wang et al. | |
| 7,262,573 B2 | 8/2007 | Wang et al. | |
| D558,351 S | 12/2007 | Diener et al. | |
| 7,571,336 B2 | 8/2009 | Barthe et al. | |
| 7,640,866 B1 | 1/2010 | Schermerhorn | |
| 7,884,735 B2 | 2/2011 | Newkirk | |
| 8,401,275 B2 | 3/2013 | Wang et al. | |
| 8,515,577 B2 | 8/2013 | Wang et al. | |
| 8,799,011 B2 | 8/2014 | Wilson et al. | |
| 9,265,680 B2 | 2/2016 | Sharps et al. | |
| 9,901,503 B2 | 2/2018 | Christensen et al. | |
| 10,075,214 B2 | 9/2018 | Howell et al. | |
| 10,938,446 B2 * | 3/2021 | Howell | H02J 7/0042 |
| 2004/0138547 A1 | 7/2004 | Wang et al. | |
| 2006/0034427 A1 | 2/2006 | Brooks | |
| 2006/0179571 A1 | 8/2006 | Newkirk | |
| 2007/0021871 A1 | 1/2007 | Wang et al. | |
| 2007/0183588 A1 | 8/2007 | Bailey et al. | |
| 2007/0189462 A1 | 8/2007 | Spahn | |
| 2007/0210917 A1 | 9/2007 | Collins et al. | |
| 2008/0172789 A1 | 7/2008 | Elliot et al. | |
| 2008/0235872 A1 | 10/2008 | Newkirk et al. | |
| 2008/0240358 A1 | 10/2008 | Utschig et al. | |
| 2009/0125147 A1 | 5/2009 | Wang et al. | |
| 2011/0205061 A1 | 8/2011 | Wilson et al. | |
| 2011/0213210 A1 | 9/2011 | Temby et al. | |
| 2011/0245973 A1 | 10/2011 | Wang et al. | |
| 2011/0277242 A1 | 11/2011 | Dionne et al. | |
| 2011/0288417 A1 | 11/2011 | Pinter et al. | |
| 2012/0025991 A1 | 2/2012 | O'Keefe et al. | |
| 2012/0029697 A1 | 2/2012 | Ota et al. | |
| 2012/0095604 A1 | 4/2012 | Alexanian | |
| 2012/0117730 A1 | 5/2012 | Lemire et al. | |
| 2015/0081335 A1 | 3/2015 | Dixon et al. | |
| 2016/0013837 A1 | 1/2016 | Howell et al. | |

FOREIGN PATENT DOCUMENTS

| | | |
|---|---|---|
| JP | 2012023841 A | 2/2012 |
| WO | 2014164248 A1 | 10/2014 |

\* cited by examiner

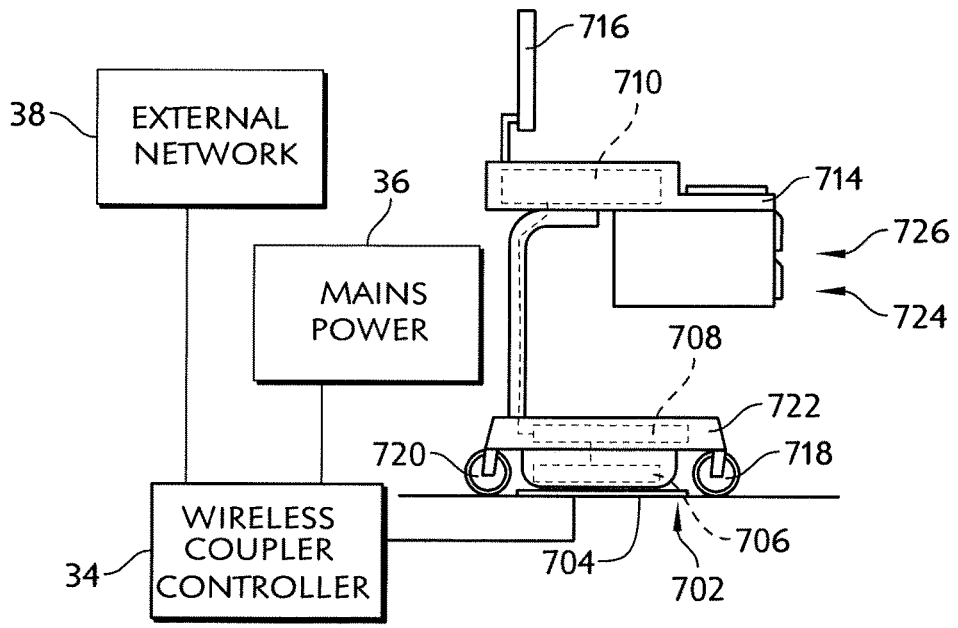
FIG. 20
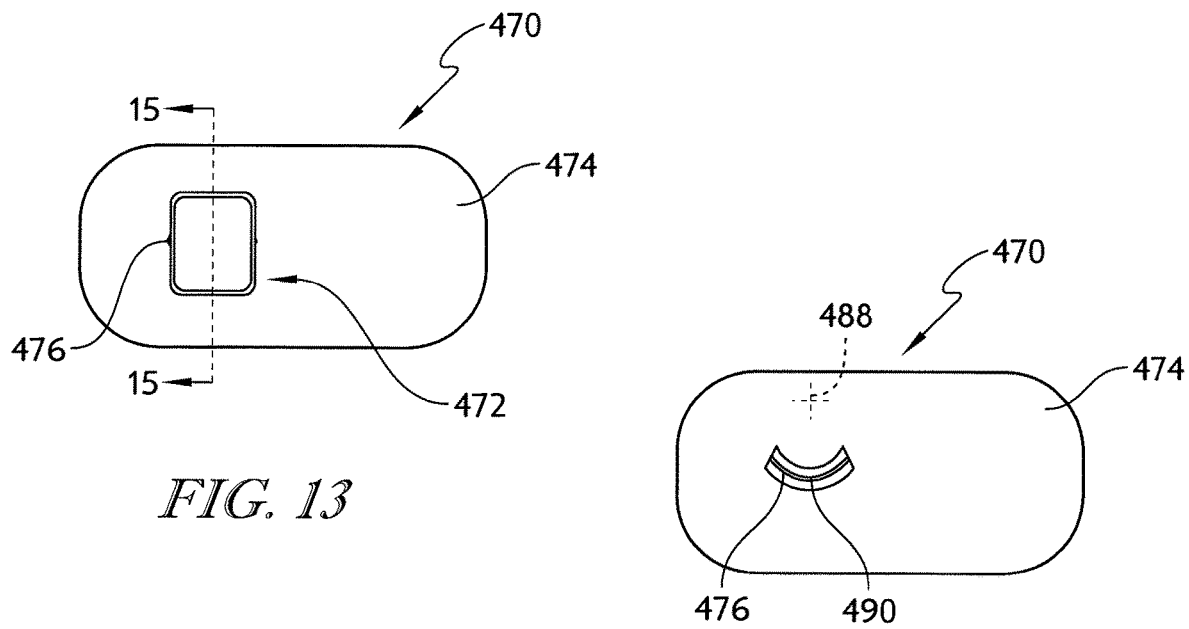
FIG. 13
FIG. 14

WIRELESS BED POWER

PRIORITY CLAIM

This application is a continuation of U.S. application Ser. No. 16/122,013, filed Sep. 5, 2018, which is a continuation of U.S. application Ser. No. 14/771,929, filed Sep. 1, 2015, which is a U.S. National Counterpart Application of International Application Serial No. PCT/US2014/021507 filed Mar. 7, 2014, which claims, under 35 U.S.C. § 119(e), the benefit of and priority to U.S. Provisional Application No. 61/776,169 filed Mar. 11, 2013, which are expressly incorporated by reference herein.

BACKGROUND

The present disclosure is related to power and communication in patient support apparatuses. More specifically, the present disclosure is related to a patient support apparatus or accessory that receives power and communication from an adjacent structure with no physical connection between the apparatus and the structure.

Patient care equipment such as hospital beds, and auxiliary carts and devices in a patient room are each becoming more sophisticated. The patient care equipment has become more sophisticated allowing information about the equipment or a patient related to the equipment to be transmitted to a central information system and made part of a particular patient's medical record. Mobility of the equipment is important to the provision of care so that the equipment can move with the patient as the patient moves through a hospital to receive care.

The use of battery powered equipment is acceptable, but charging of the batteries generally requires that the equipment be physically connected to mains power through a power cord. When necessary, a caregiver must position the equipment in the room and plug a cord into a wall. The location of the power outlet may be behind the preferred position of the equipment such that a caregiver must move the equipment multiple times to get access to the outlet and return the equipment to the preferred location after a cord is connected. The cord hangs from the equipment when not in use and presents a trip hazard.

Additionally, communications between the equipment and the central information system may be accomplished through either a wired or wireless datalink, but association of the particular piece of equipment and a particular patient is problematic. In a wired datalink, the connection point of the datalink may be associated with a patient location. Furthermore, a wired datalink may also create additional logistic issues similar to the problems associated with a power cord including the need to connect the datalink and the trip hazard presented by the wired datalink. A wireless datalink creates challenges in that the location of the equipment may not be readily distinguished as several different receiving points may simultaneously detect the same signal.

SUMMARY

The present application discloses one or more of the features recited in the appended claims and/or the following features which, alone or in any combination, may comprise patentable subject matter:

According to a first aspect of the present disclosure, a system comprises a patient support apparatus, an architectural unit, a power supply, a communications system and an interface. The patient support apparatus includes a control system. The power supply is coupled to the architectural unit and is operably coupled to a mains power supply. The communication system is operably coupled to an information system. The interface is in electrical communication with the communication system and the power supply. The interface is operable to simultaneously provide power and a communications signal to the patient support apparatus to directly power at least one subsystem of the patient support apparatus while concurrently transferring data between the communication system and the control system of the patient support apparatus without physical contact therebetween.

In some embodiments, the interface includes a first portion positioned on the architectural unit and a second portion supported on the patient support apparatus.

In some embodiments, the control system of the patient support apparatus is operable to detect that the second portion is powered. In some embodiments, the control system of the patient support apparatus is operable to initialize the operation of the control system utilizing the power transferred through the interface. In some embodiments, the initialization of the operation of the control system includes initiating communication between the control system and the communication system. In some embodiments, the initialization of the operation of the control system includes aligning the first portion and the second portion of the interface to optimize the efficiency of the interface. In some embodiments, aligning the first portion and the second portion includes moving the first portion to an optimized position. In some embodiments, aligning the first portion and the second portion includes moving the first portion in first axis. In some embodiments, aligning the first portion and the second portion includes moving the first portion in a second axis. In some embodiments, aligning the first portion and the second portion includes moving the first portion in a third axis. In some embodiments, aligning the first portion and the second portion includes moving the second portion to an optimized position. In some embodiments, aligning the first portion and the second portion includes moving the second portion in first axis. In some embodiments, aligning the first portion and the second portion includes moving the second portion in a second axis. In some embodiments, aligning the first portion and the second portion includes moving the second portion in a third axis.

In some embodiments, aligning the first portion and the second portion includes moving the second portion to an optimized position.

In some embodiments, aligning the first portion and the second portion includes varying a position of the first portion according to a search algorithm that maximizes efficiency of the interface.

In some embodiments, aligning the first portion and the second portion includes performing a search algorithm to align an optical detector on one of the first portion and the second portion with an optical emitter positioned on the other of the first portion and the second portion. In some embodiments, aligning the first portion and the second portion includes varying a position of the first portion to align an optical detector on one of the first portion and the second portion with an optical emitter positioned on the other of the first portion and the second portion. In some embodiments, aligning the first portion and the second portion includes varying a position of the second portion to align an optical detector on one of the first portion and the second portion with an optical emitter positioned on the other of the first portion and the second portion.

In some embodiments, aligning the first portion and the second portion includes performing a search algorithm to align an optical detector on one of the first portion and the second portion with indicia positioned on the other of the first portion and the second portion.

In some embodiments, aligning the first portion and the second portion includes varying a position of the second portion to align an optical detector on one of the first portion and the second portion with indicia positioned on the other of the first portion and the second portion.

In some embodiments, the interface comprises a wireless communications bus connection. In some embodiments, the control system of the patient support apparatus comprises a communications bus that is compatible with the communications bus of the interface. In some embodiments, the communications system comprises a communications bus that is compatible with the communications bus of the interface. In some embodiments, the communications bus of the interface transfers data between the communications system and the control system of the patient support apparatus. In some embodiments, the communications bus of the interface is RS-438 compatible. In some embodiments, the communications bus of the interface is a CAN bus.

In another aspect of the present disclosure, a patient support apparatus comprises a first member, a second member movable relative to the first member, and a first wireless coupler. The first wireless coupler includes a first portion positioned on the first member and a second portion position on the second member. The first wireless coupler is operable to transfer electrical power from the first portion to the second portion throughout the range of motion of the second member as the second member moves between a first position and a second position relative to the first member.

In some embodiments, the second member comprises a side rail.

In some embodiments, the second member comprises a user interface and the first member comprises a side rail.

In some embodiments, the patient support apparatus further comprises a third member supported from the second member and movable relative to the second member. The second wireless coupler is operable to transfer electrical power from the second member to the third member throughout the range of motion of the third member as the third member moves between a first position and a second position relative to the second member. In some embodiments, the first member includes a first receiver operable to receive wireless power from an architectural structure spaced apart from the patient support apparatus, the power received by the first receiver being used to power components on the third member in real time during operation of the patient support apparatus.

In another aspect of the present disclosure, a patient support apparatus comprises a barrier, and a user interface supported from the barrier, the user interface responsive to movement of the barrier relative to gravity to maintain the user interface in a first orientation throughout the range of movement of the barrier.

In some embodiments, gravity acts on the user interface to maintain user interface in the first orientation.

In some embodiments, the patient support apparatus further comprises a motor positioned on the barrier and engaged with the user interface, the motor operable to move the user interface during movement of the barrier to maintain the user interface in the first orientation. In some embodiments, the patient support apparatus further comprises a controller coupled to the motor and an accelerometer coupled to the controller. The accelerometer provides a signal indicative of the orientation of the barrier. The controller modifies the position of the user interface relative to the barrier by operating the motor to maintain the user interface in the first orientation regardless of the position of the barrier. In some embodiments, the user interface includes a pivot received in a journal on a body of the barrier, the pivot movable within the journal to prevent movement between the user interface and the barrier. In some embodiments, the pivot includes a plurality of conductors positioned on at least a portion of the periphery of the pivot, each conductor spaced apart from an adjacent conductor along a longitudinal length of the pivot and coupled to circuitry supported in the user interface. In some embodiments, the barrier further includes a plurality of brushes, each brush positioned to engage one of the conductors of the pivot, each brush an annular conductor forming a first electrical circuit that is maintained throughout the range of motion of the user interface relative to the barrier.

According to another aspect of the present disclosure, a system for powering an article of patient care equipment comprises an article of patient care equipment, a plurality of batteries, a battery receiver, a charging mat and means for causing a first of the plurality of batteries to be received in the battery receiver while a second of the batteries is positioned in the battery receiver, the first and second batteries simultaneously powering the electrical circuitry. The patient care equipment includes a frame and electrical circuitry. The battery receiver is supported from the frame. The battery receiver has a first end and a second end and is configured to frictionally grip at least one of the batteries. The charging mat is positioned on a floor and operable to support at least one of the plurality of batteries and charge the battery while the battery is supported on the charging mat.

In some embodiments, the system further comprises means for causing the second battery to be ejected. In some embodiments, the first battery acts on the second battery to urge the second battery out of the battery receiver. In some embodiments, the means for causing a first of the plurality of batteries to be received in the battery receiver while a second of the batteries is positioned in the battery receiver comprises a retractable barrier supported on the floor, the first battery engaging the barrier as the article of patient care equipment moves over the floor.

In some embodiments, the plurality of batteries have positive and negative terminals that engage the battery receiver when the batteries are frictionally gripped by the battery receiver.

In some embodiments, the battery receiver includes guides positioned at the first end.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which:

FIG. 13 is a plan view of another embodiment of a side rail having a user interface that is movable relative to the side rail body to maintain user interface in a generally vertical orientation for ease-of-use by a caregiver;

FIG. 14 is a plan view of the body of the side rail of FIG. 13 with the user interface omitted;

FIG. 20 is a diagrammatic view of a healthcare cart positioned such that a transmitter on the floor of a room cooperates with a receiver on the cart to form a wireless coupler operable to transfer power and/or data between the transmitter and the receiver;

DETAILED DESCRIPTION OF THE DRAWINGS

Figure 1:
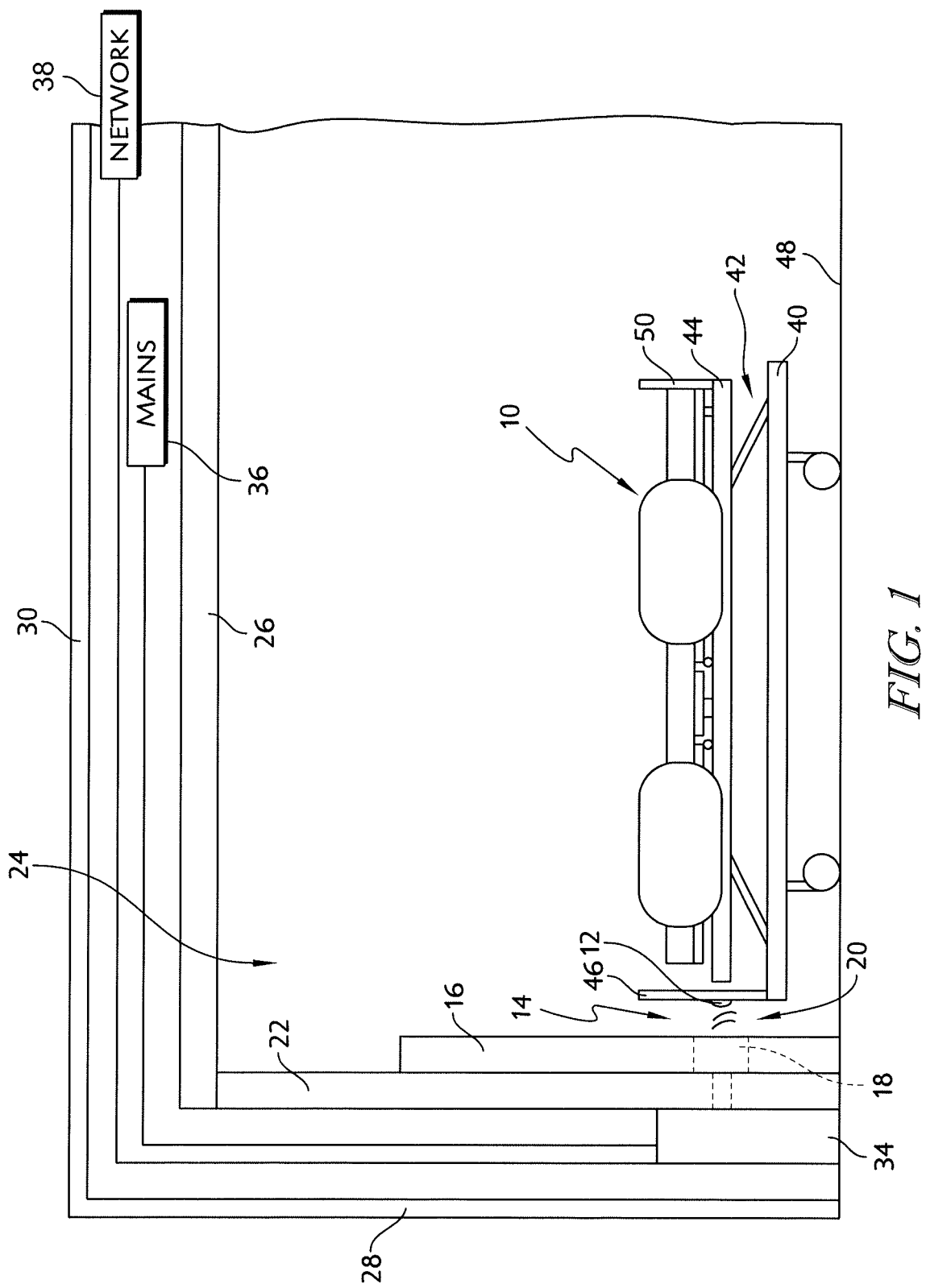
FIG. 1 is a diagrammatic representation of a patient support apparatus positioned in a hospital room such that a wireless coupler transfers data and/or power between a transmitter on an architectural structure in the room and receiver on the patient support apparatus.

In one embodiment of a patient support apparatus 10, illustratively embodied as a bed, the patient support apparatus 10 includes a receiver 12 that simultaneously receives power and data over a wireless datalink 14. When the receiver 12 is placed in proximity to a transmitter 18 positioned on an architectural structure 16, such as a medical headwall, for example, the transmitter 18 is operable to detect the presence of the receiver 12 and to initiate the transfer of power and/or data over the wireless datalink 14.

The transmitter 18 and receiver 12 cooperate to define a wireless coupler 20 that is illustratively embodied as a Proxi-Point™ apparatus available from PowerbyProxi™, Inc. of Pleasanton, Calif. When the patient support apparatus 10 is moved into proximity of the medical headwall 16, the transmitter 18 senses the presence of the receiver 12 and begins the wireless transmission of power and/or data over link 14. In some embodiments, the transmitter 18 continuously generates power waves that, when in the range of receiver 12, cause receiver 12 to become powered, allowing receiver 12 to generate an identification signal to the transmitter 18 so that the transmitter 18 becomes aware that the wireless coupler 20 is operational. In some embodiments, the receiver 12 generates a wireless signal when power is received. When the wireless signal is received by the transmitter 18, the transmitter 18 initiates communications with the receiver 12.

The medical headwall 16 is positioned adjacent a studded wall 22 of a hospital room 24. The hospital room 24 also includes a suspended ceiling 26. As shown diagrammatically in the illustrative embodiment of FIG. 1, a structural wall 28 is spaced apart from the studded wall 22 to form a space therebetween. Similarly, a structural ceiling 30 is positioned above the suspended ceiling 26 such that a space is formed between the structural ceiling 30 and the suspended ceiling 26. A service line 32 is positioned in the space between the ceilings 26, 30 and the walls 22, 28 so that mains power supply is routed to an wireless coupler controller 34 positioned in the service space between the walls 22, 28, the wireless coupler controller 34 providing operational power to the transmitter 18. A separate, hardwired communications bus may also be positioned in the service line 32 to transfer a communications signal between the transmitter 18 and an network 38. In some embodiments, the communications bus of the interface is RS-438 compatible. In some embodiments, the communications bus of the interface is a CAN bus.

The patient support apparatus 10 illustratively includes a lower frame 40, a lift system 42, and an upper frame 44 which is movable vertically relative to the lower frame 40 when the lift system 42 is actuated. In the illustrative embodiment shown diagrammatically in FIG. 1, the receiver 12 is mounted to a headboard 46 which is supported from the lower frame 40 which causes the receiver 12 to be maintained in a fixed vertical position relative to a floor 48 of the hospital room 24. In this embodiment, the vertical position of the transmitter 18 is fixed relative to the floor 48 such that there is no need for adjustment of the vertical position of either the transmitter 18 or receiver 12. It should be understood that in other embodiments the headboard 46 may be mounted to the upper frame 44 in a manner similar to a foot board 50 shown in FIG. 1. As will be discussed in further detail below, when the receiver is mounted to the movable upper frame 44, the vertical position of the upper frame 44 may be changed to facilitate vertical alignment of the transmitter 18 and receiver 12.

Figure 2:
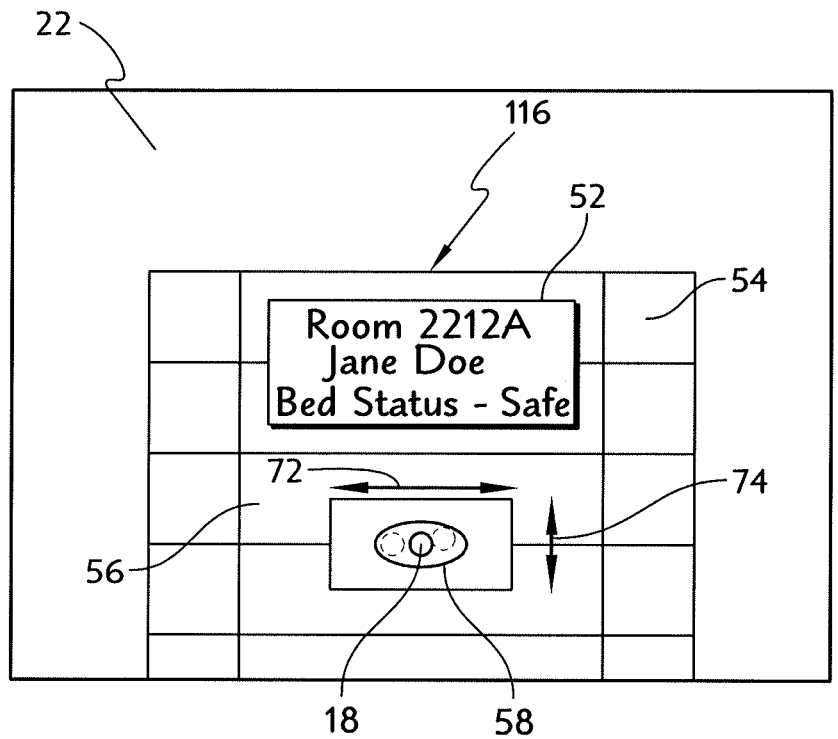
FIG. 2 is a diagrammatic representation of a wall of a hospital room that includes a studded wall and an architectural structure positioned adjacent the studded wall, the architectural structure supporting a wireless power/data transmitter and a display panel for displaying status of the patient and patient support apparatus associated with the architectural structure.

Referring now to FIG. 2, an embodiment of a medical headwall 116 is shown diagrammatically positioned adjacent a wall 22. The medical headwall 116 includes a display panel 52 which is operable to display information related to the patient support apparatus 10 and a patient supported on the patient support apparatus 10 which has been associated with a particular location in a healthcare facility. For example, the room number and location is displayed along with a patient name and the status of the patient support apparatus 10. In other embodiments, other information or statuses may also be displayed on the display panel 52. The medical headwall 116 includes a number of panels 54, 56 which provide an architectural effect as is known in the art. The structure of the medical headwall 116 may include embodiments such as those disclosed in U.S. Patent Application Publication No. 20120/0095604 entitled "MODULAR ARCHITECTURAL ROOM SYSTEM," which is incorporated in its entirety be reference herein. The transmitter 18 is positioned in an aperture 58 and is movable between a plurality of positions as suggested by the positions shown in broken lines in FIG. 2. Movement of the transmitter 18 in the aperture 58 permits adjustment of the transmitter 18 to a location in which it is aligned with the receiver 12 positioned on the patient support apparatus 10. Alignment of the transmitter 18 and the receiver 12 optimizes the transfer of power and data between the transmitter 18 and receiver 12.

Figure 3:
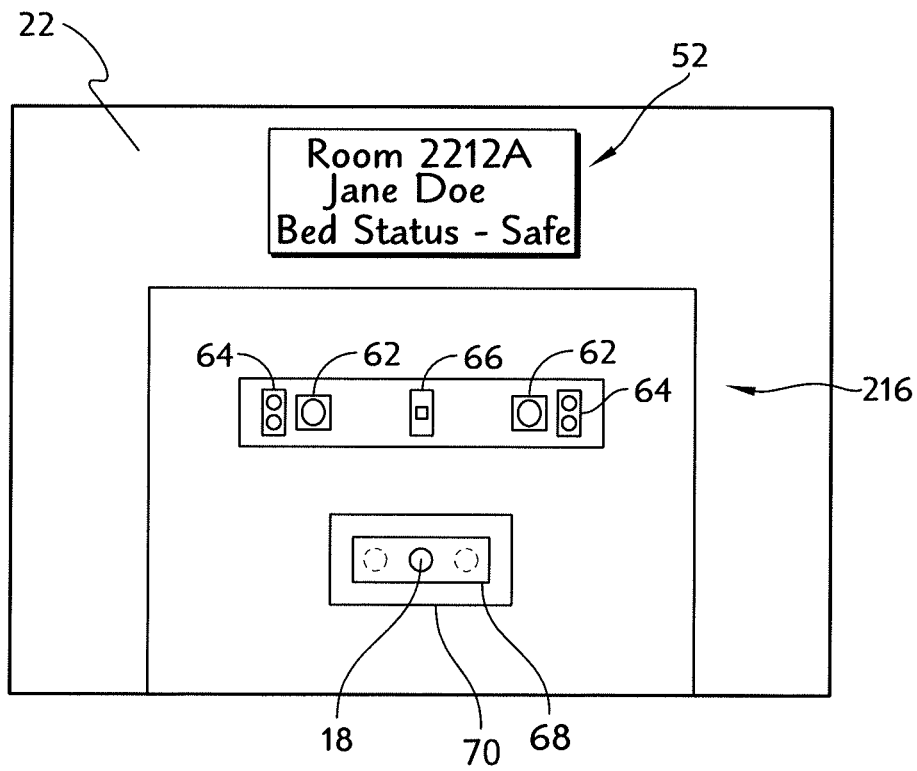
FIG. 3 is a diagrammatic representation of a wall of the hospital room that includes a studded wall and an architectural structure supporting another embodiment of a wireless power/data transmitter as well as a panel of medical service outlets, the hospital room including a display panel for displaying the status of the patient and patient support apparatus associated with the architectural structure, the display panel supported on the studded wall.

In another embodiment shown in FIG. 3, display panel 52 is mounted directly to wall 22 above another embodiment of medical headwall 216. Medical headwall 216 includes a panel 60 which may include one or more service outlets such as a medical gas outlet 62, a power outlet 64, or a data port 66. In the illustrative embodiment of FIG. 3, the transmitter 18 is positioned in a horizontally oriented aperture 68 in a panel 70 on the medical headwall 216. In the illustrative embodiment of FIG. 3, transmitter 18 is movable horizontally within the aperture 68 to plurality of positions as suggested by the positions shown in broken lines in FIG. 3. In the embodiment of FIG. 3, transmitter 18 is movable manually to align transmitter 18 with a receiver 12 on the patient support apparatus 10. Because the receiver 12 is in a fixed position vertically and the transmitter 18 is in a fixed position vertically, there is no need for vertical alignment therebetween. However, the horizontal alignment permits a caregiver to simply position the patient support apparatus 10 near the transmitter 18 and slide the transmitter 18 to align the position of the transmitter 18 with the receiver 12.

It should be understood that the aperture 58 of the embodiment of FIG. 2 may be modified to a shape other than an elliptical shape to compensate for other ranges of adjustment that might be necessary. The transmitter 18 may be moved in a lateral direction as indicated by an arrow 72 or a vertical direction as indicated by an arrow 74 in FIG. 2.

Figure 4:
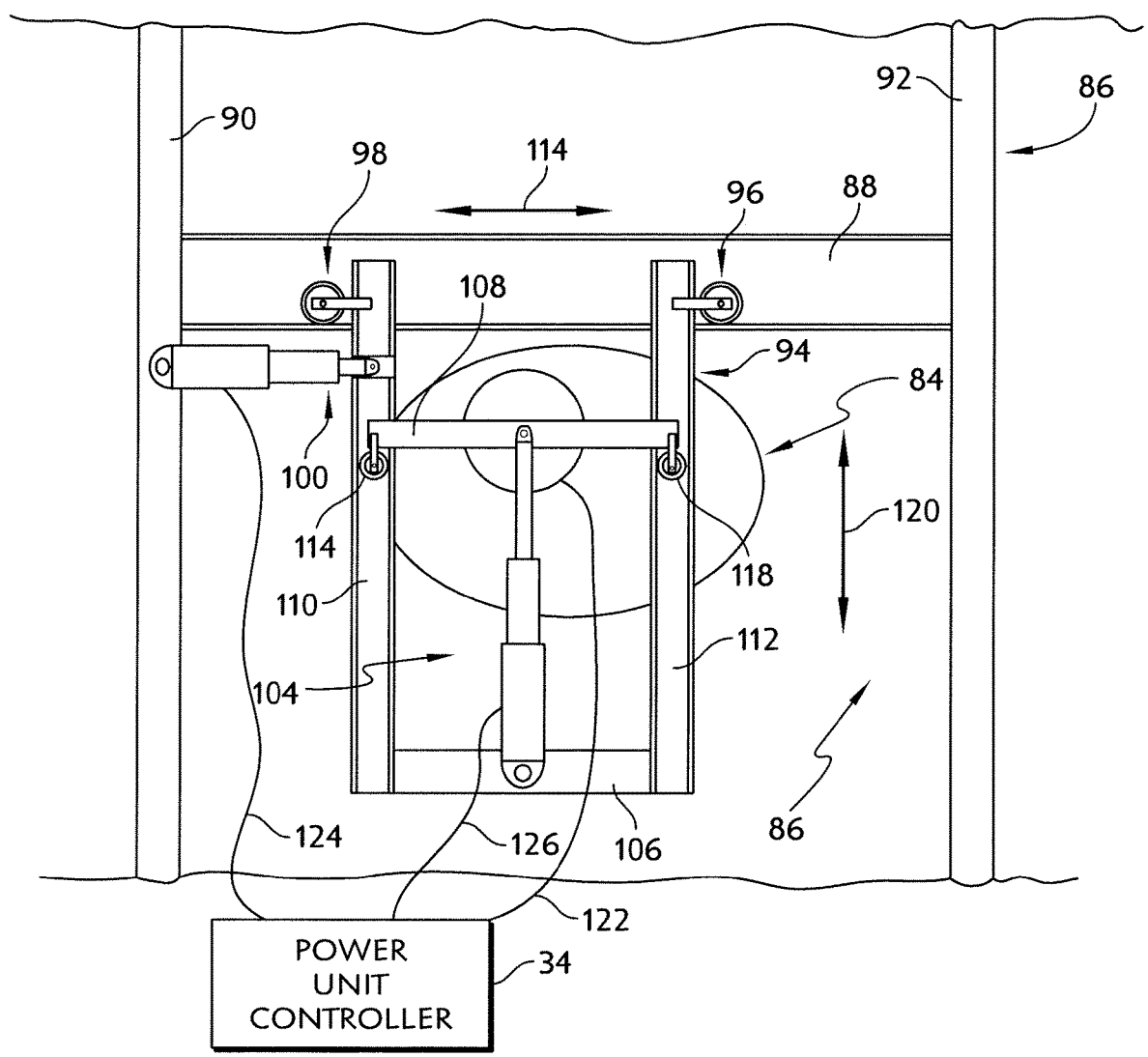
FIG. 4 is a plan view of a frame structure of an architectural structure viewed from the backside of the architectural structure, the frame supporting an adjustment mechanism operable to adjust the position of a power/data transmitter supported on the architectural structure.

Referring now to FIG. 4, the position of the transmitter 18 may be adjusted both vertically and laterally by an adjustment mechanism 84 that is supported from a frame 86 of the medical headwall 116. The adjustment mechanism 84 is suspended from a crossbeam 88 that spans between two vertical frame members 90 and 92 of the medical headwall 116. The adjustment mechanism includes a frame 94 that is supported from the crossbeam 88 by a pair of rollers 96 and 98. An actuator 100 is coupled to the frame 94 and the vertical frame member 90 such that extension and retraction of the actuator 100 as indicated by arrow 102 causes lateral movement of the frame 94 and thereby the transmitter 18 to adjust the position of the transmitter 18. Similarly, an actuator 104 is coupled to a horizontal cross member 106 of the frame 94 at one end. A cross beam 108 is coupled to the transmitter 18 and engages a first frame member 110 and a second frame member 112 of the adjustment mechanism 84 by respective rollers 114 and 118. Extension and retraction of the actuator 104 as indicated by the arrow 120 causes movement of the transmitter 18 vertically. The transmitter 18 is coupled to the wireless coupler controller 34 by a flexible cord 122. The actuator 100 receives power from the wireless coupler controller 34 through a cord 124 and the actuator 104 receives power from the wireless coupler controller 34 through a flexible cord 126.

Figure 5:
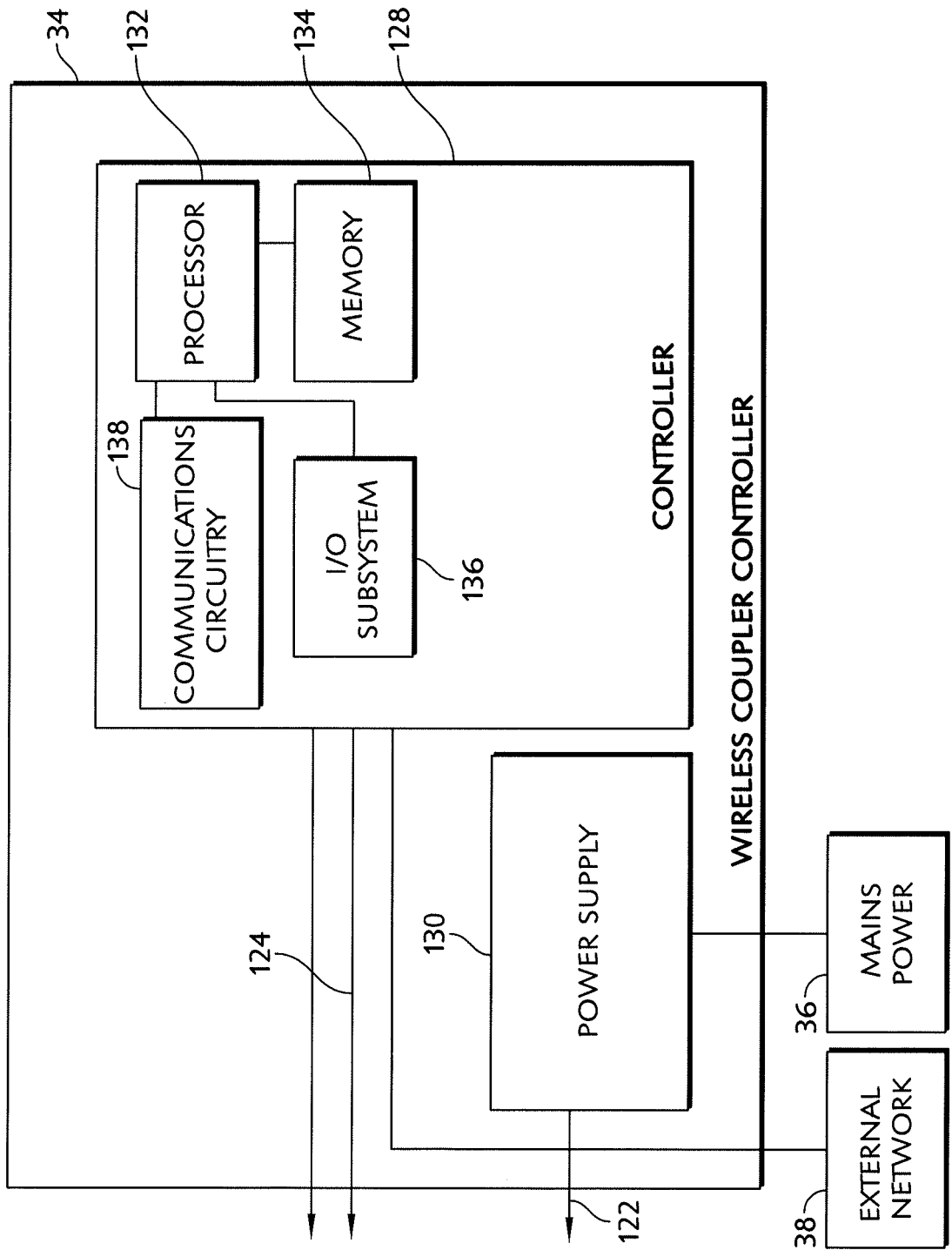
FIG. 5 is a block diagram of a power control unit for a wireless coupler, the power control unit including a power supply and a controller.

As shown diagrammatically in FIG. 5, the wireless coupler controller 34 includes a controller 128 and a power supply 130. The power supply 130 is coupled to the mains power 36 and is operable to provide power to the transmitter 18 as required to operate the wireless coupler 20. The power supply 130 is under control of the controller 128 which includes a processor 132 coupled to a memory device 134. The memory device 134 includes the instructions used by the processor 132 to operate the wireless coupler 20. The processor is also in communication with an I/O subsystem 136 that is coupled to the network 38 and communicates with the patient support apparatus 10 through the wireless coupler 20. The I/O subsystem 136 operates communications circuitry 138 that provides the communications interface between the transmitter 18 and the I/O subsystem 136. In some embodiments, the I/O subsystem 136 may be omitted and the processor 132 may control the communication circuitry 138 directly. However, in embodiments where the I/O subsystem 136 is present, the I/O subsystem 136 may act as a translator between the communication circuitry 138 of the wireless coupler controller 34 and the network 38. The I/O subsystem 136 may communicate using a first protocol with the network 38 while the transmitter 18 utilizes a second protocol with the communications circuitry 138.

In addition the I/O subsystem 136 is operable to control the actuators 100 and 104 through respective cords 124 and 126. In some embodiments, the power supply 130 is operable to provide feedback to the processor 132 regarding the efficiency of power transfer from the power supply 130 through the transmitter 18 to the receiver 12. The processor 132 may operate the adjustment mechanism 84 to search for the position of the transmitter 18 which maximizes the efficiency of the power transfer between the transmitter 18 and receiver 12.

Figure 6:
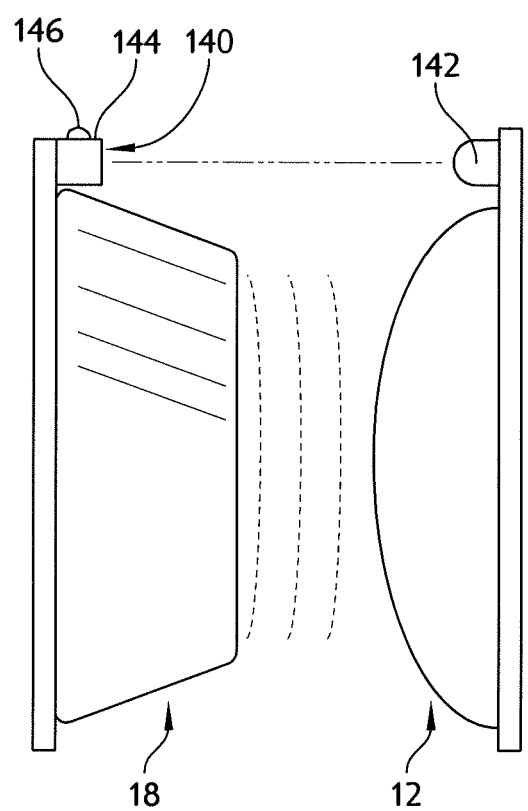
FIG. 6 is a diagrammatic representation of a structure used to identify that the transmitter and receiver of a wireless power/data coupler is properly aligned.

Referring now to FIG. 6, the wireless coupler 20 may further include an optical detector 140 positioned adjacent the transmitter 18 and an emitter 142 positioned adjacent the receiver 12, the emitter 142 providing a directed light signal that when detected by the optical detector 140 indicates that the transmitter 18 and receiver 12 are properly aligned. When the detector 140 and emitter 142 are present, the processor 132 may move the transmitter 18 and optical detector 140 combination in a search pattern until proper alignment of the optical detector 140 and emitter 142 is detected. In embodiments where the actuators 100 and 104 are not present, the optical detector 140 may illuminate an LED 146 on a housing 144 of the optical detector 140 to indicate proper alignment. Thus, a user may reposition the transmitter 18 until the LED 146 is illuminated to indicate proper alignment.

Figure 7:
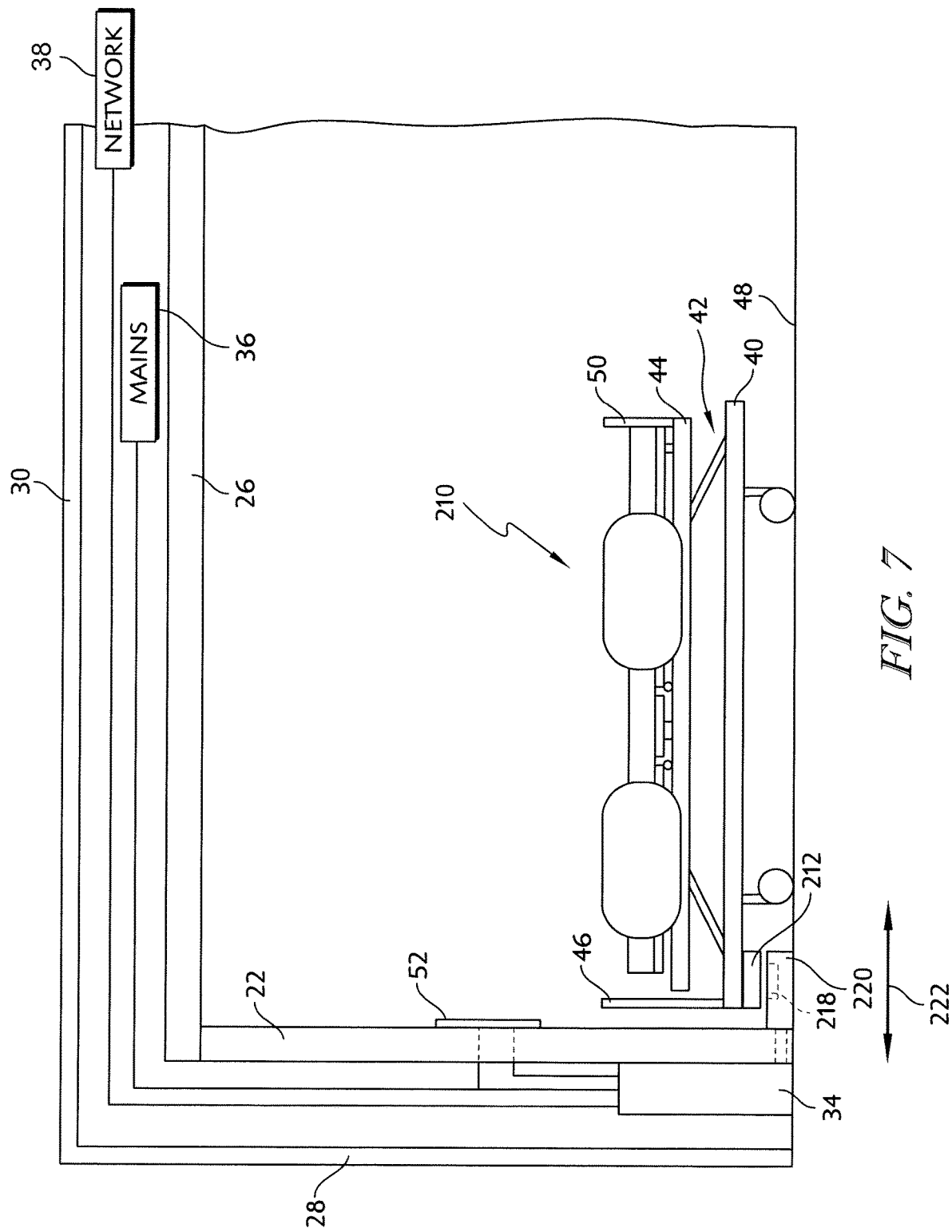
FIG. 7 is a diagrammatic representation of another embodiment of patient support apparatus positioned in a hospital room such that a wireless coupler transfers data and/or power between a transmitter on a floor of the room and receiver on the patient support apparatus.

In another embodiment shown diagrammatically in FIG. 7, a patient support apparatus 210 is similar to the patient support apparatus 10, however patient support apparatus 210 includes a receiver 212 positioned on the lower side of the lower frame 40. A transmitter 218 is positioned on the floor 48 adjacent the studded wall 22. In the embodiment of FIG. 7 there is no medical headwall and the patient support apparatus 210 is positioned near the studded wall 22 such that the receiver 212 is positioned over the transmitter 218. Because the lower frame 40 has a fixed vertical position relative to the floor 48, the receiver 212 maintains a fixed vertical position so that it is properly spaced from the transmitter 218. The transmitter 218 is positioned in a housing 220 and may be movable laterally (into and out of the page as shown in FIG. 7) in a manner similar to the adjustment of the embodiment of FIG. 3. The structure of the embodiment of FIG. 7 may include an adjustment mechanism 84 similar to that disclosed in the embodiment of FIG. 4, however, the orientation of the adjustment mechanism 84 would result in the transmitter 18 being moved horizontally as indicated by the arrow 222 as opposed to vertically as described in the embodiment of FIG. 3. The lateral adjustment of the transmitter 218 would be similar to that of the embodiment of FIG. 3. The wireless coupler controller 34 is electrically connected to the transmitter 218 in the adjustment mechanism 84 through the studded wall 22.

As suggested by FIG. 7, a display panel 52 is positioned on the studded wall 22 and is in communication with the wireless coupler controller 34 and the network 38. It should be understood that the display panel 52 may be similarly connected in any of the embodiments described herein.

Figure 8:
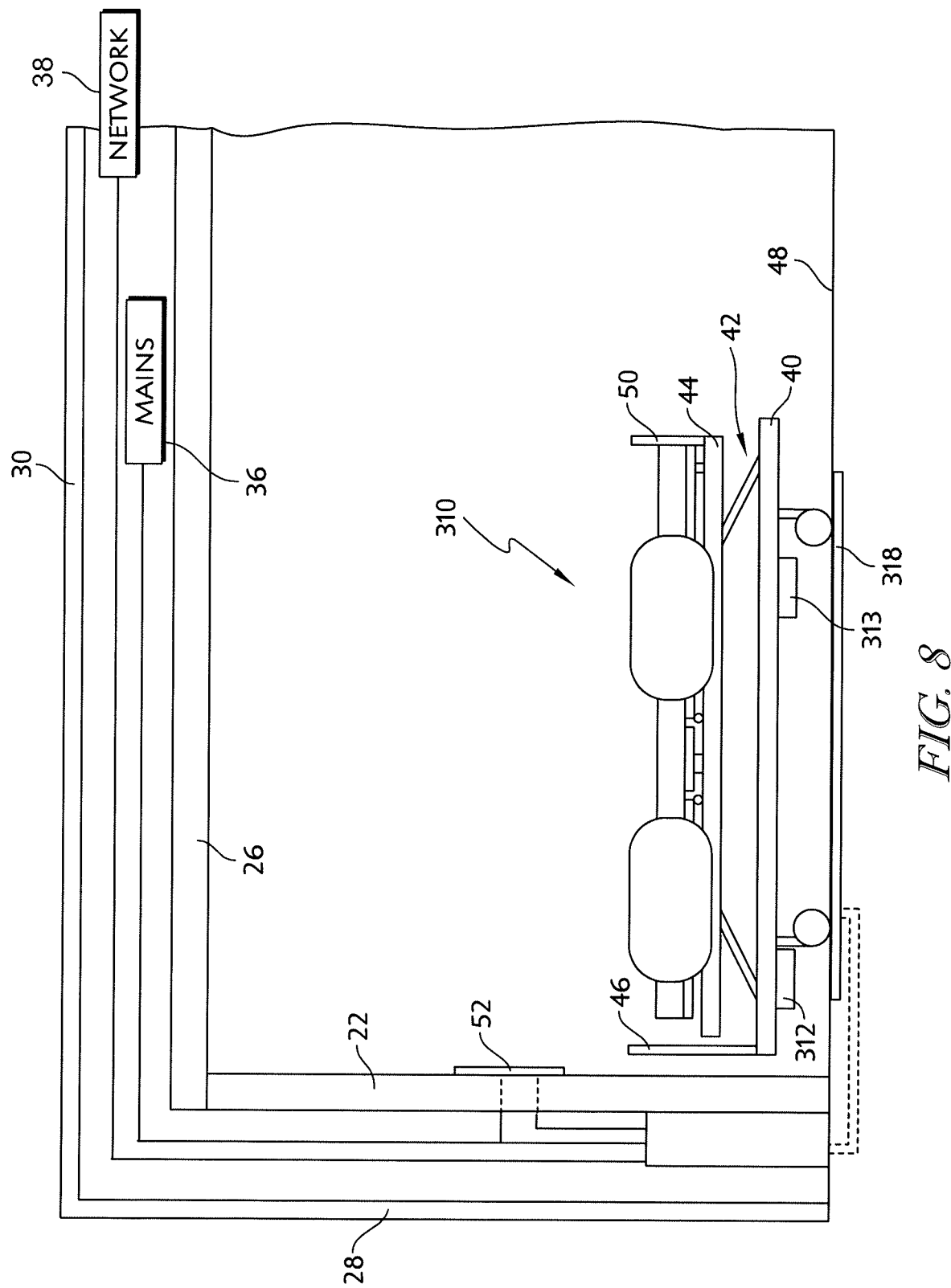
FIG. 8 is a diagrammatic representation of yet another embodiment of patient support apparatus positioned in a hospital room such that a wireless coupler that transfers data and/or power between the transmitter on a floor of the room and receiver on the patient support apparatus.

In still another embodiment shown diagrammatically in FIG. 8, a patient support apparatus 310 includes two separate receivers 312 and 313 each of which are positioned on a lower side of the lower frame 40. The transmitter 318 is embodied as a pad position in the floor 48. Again, because the receivers 312 and 313 are positioned in a fixed position vertically, the spacing between the transmitter 318 and the receivers 312 and 313 is maintained. In the embodiment of FIG. 8, there is no need to align the receivers 312 and 313 with the transmitter 318.

Each of the patient support apparatuses 10, 210, and 310 are embodied with a receiver that is operable to receive power from a respective transmitter 18, 218 or, 318. In each embodiment, the transmitter and receiver pair is also operable to allow for two way wireless communication therebetween so that the patient support apparatus may share information with the network 38. In addition, it is contemplated that the transfer of power between each transmitter and receiver pair would be sufficient to operate the respective patient support apparatus directly. In some embodiments, the power transfer may result in a transfer of power to a charging circuit of a battery system for the respective patient support apparatus with the patient support apparatus drawing from the battery system to operate. Thus the battery system would be subject to constant charging while only being depleted when the patient support apparatus actually draws power from the battery supply.

Figure 9:
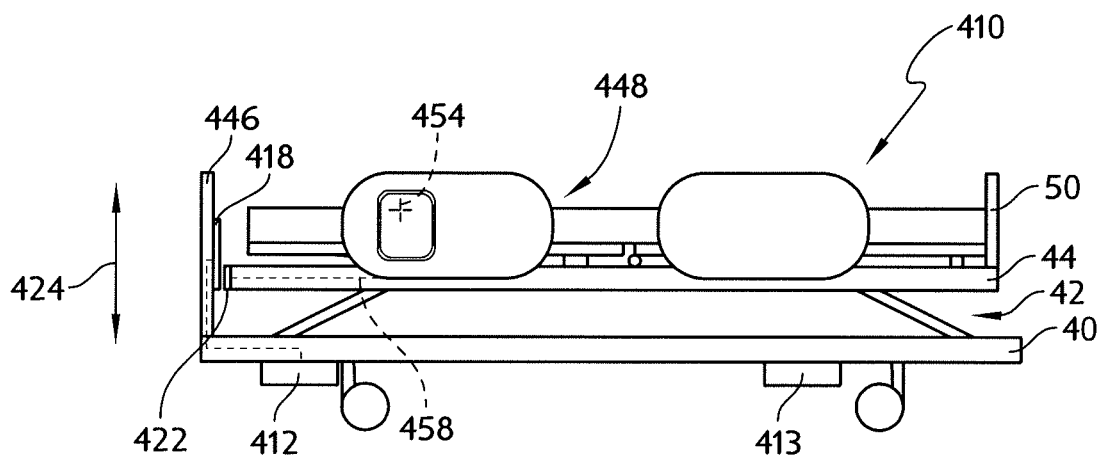
FIG. 9 is a diagrammatic representation of still yet another embodiment of the patient support apparatus that includes a transmitter of wireless power and/or data positioned on a fixed member of the patient support apparatus with a respective receiver positioned on a moving frame of the patient support apparatus.

An additional advantage of having the ability to wirelessly transmit power includes the ability, as suggested in FIG. 9, to have power transmitted across interfaces between frame members of the respective patient support apparatus. For example, a patient support apparatus 410, shown in FIG. 9, includes two separate receivers 412 and 413 similar to the receivers 312 and 313 discussed above. Circuitry in the patient support apparatus 410 permits the transfer of power from the receivers 412 and 413 to a transmitter 418 positioned on a headboard 446 of the patient support apparatus 410. The transmitter 418 then transfers the power to a receiver 422 positioned on the upper frame 444 of the patient support apparatus 410. The transmitter 418 is structured similarly to the transmitter 318 discussed above such that movement of the upper frame 444 vertically as indicated by arrows 400 by the arrow 424 maintains the receiver 422 adjacent the transmitter 418 so that power is transferred to the upper frame 444 regardless of the position of the upper frame relative to the lower frame 40.

Figure 10:
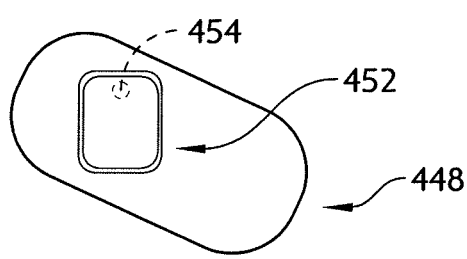
FIG. 10 is a diagrammatic representation of a side rail of the patient support apparatus of FIG. 9 in an inclined orientation due to movement of one of the members of the patient support apparatus, a user interface of the side rail being maintained in a generally vertical orientation relative to a body of the side rail due to the force of gravity acting on the user interface thereby causing the user interface to pivot relative to the body of the side rail.

The patient support apparatus 410 includes a side rail 448. The side rail 448 is mounted to a head section 450 supported on the upper frame 444 and pivotable relative to the upper frame 444. A user interface 452 supported from the side rail 448 is pivotable relative to the side rail 448 about an axis 454. Pivoting of the head section 450 relative to the upper frame 444 causes the side rail 448 to pivot as suggested in FIG. 10. Because the user interface 452 is pivotable about the axis 454 the weight of the user interface 452 causes the user interface 452 to rotate about the axis 454 so that the user interface maintains a generally vertical orientation throughout the range of motion of the head section 450 and side rail 448.

Figure 11:
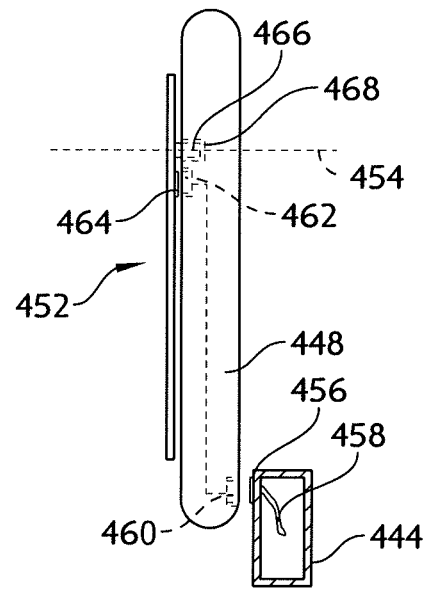
FIG. 11 is an end view of the side rail of FIG. 9 with a wireless power/data receiver on the side rail position adjacent a wireless power/data transmitter on an upper frame of the patient support apparatus.

Referring now to FIG. 11, it can be seen that a portion of upper frame 444 shown in cross-section supports a transmitter 456 which receives power through an electrical connection 459. A receiver 460 embedded in the body of the side rail 448 is operable to transfer the power and data received from the transmitter 456 to a transmitter 462 positioned in the body of the side rail 448 behind the user interface 452. A receiver 464 is positioned on the back of the user interface 452 and operable to transfer power and data to circuitry in the user interface 452. In the illustrative embodiment of FIGS. 9-11, the user interface 452 is a graphical interface including touch screen technology. In other embodiments, the user interface 452 may include one or more LED displays and traditional momentary switches in place of, or cooperating with, the graphical interface with touch screen technology. The user interface 452 is supported on a pivot 466 supported in a socket 468 formed in the body of the side rail 448. It should be understood that any of a number of bearings known in the art may be implemented to facilitate rotation of the user interface 452 relative to the body of the side rail 448.

Figure 12:
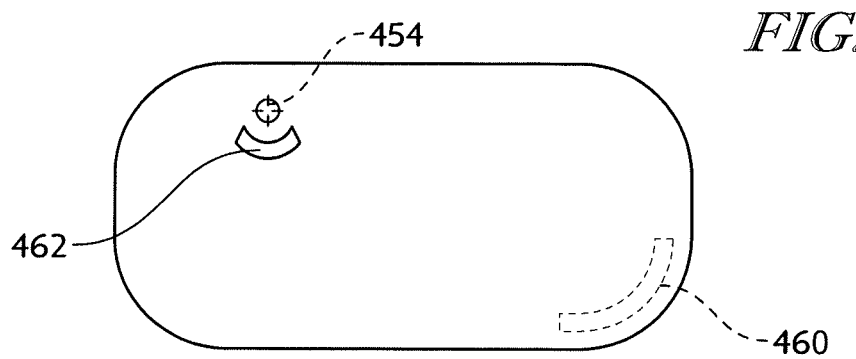
FIG. 12 is a plan view of the body of the side rail of FIGS. 9-11.

The body of the side rail 448 is shown in a plan view in FIG. 12. The transmitter 462 has an arcuate shape centered on the axis 454 so that as the receiver 464 pivots with the user interface 452 about the axis 454 the receiver 464 is continuously positioned adjacent at least a portion of the transmitter 462. Similarly, receiver 460 has an irregular shape that is configured to maintain at least a portion of the receiver 460 adjacent the transmitter 456 during movement of the side rail 448. In some embodiments, the movement of the side rail 448 may not follow a specifically circular path during movement of the head section 450 from a lowered position as shown in FIG. 9 to a raised position. In some embodiments, the pivot axis 458 of the head section 450 may move along the upper frame 444 as indicated by an arrow 471. This compound pivoting and translating motion is known in the art to reduce shear on the skin at the patient's hips when the head section 450 is raised. Thus, the shape of the receiver 460 maybe specifically configured to follow the compound motion that occurs with movement of the head section 450 between the lowered and raised positions.

Figure 15:
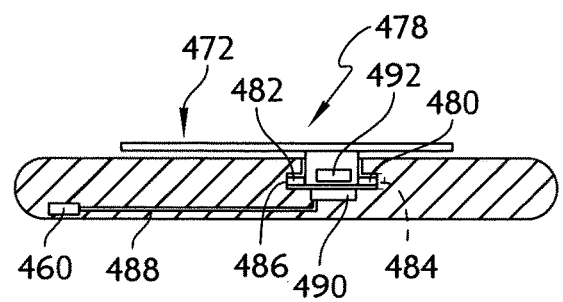
FIG. 15 is a cross-sectional view of the side rail of FIG. 13 taken along lines 15-15 of FIG. 13.

Another embodiment of side rail 470 is shown in FIG. 13 and includes a user interface 472 which is movable relative to the body 474 of the side rail 470. The body 474 is formed to include a channel 476 (best seen in FIG. 14) which receives a carriage 478 (shown in FIG. 15). The carriage 478 engages the channel 476 with rollers 480 and 482 of the carriage 478 rolling along surfaces 484 and 486 of the channel 476. Similar to the embodiment of FIGS. 9-12, the user interface 472 will pivot about an imaginary axis 488 as the side rail 470 moves with a head section 450 of a patient support apparatus. The user interface 472 has a portion which depends from the carriage 478 such that gravity acts on the user interface 472 to cause the user interface 472 to move in a channel 476 as the side rail 470 moves with the head section 450. In the embodiment of FIG. 15, a receiver 460 is positioned in the body 474 as described above with regard to the embodiment of FIGS. 9-12. The receiver 460 is in communication with a transmitter 490 through a cable 489. The transmitter 490 is in a fixed position in the channel 476 and operable to transfer power and data to a receiver 492 positioned in the carriage 478 and in communication with circuitry in the user interface 472.

Figure 16:
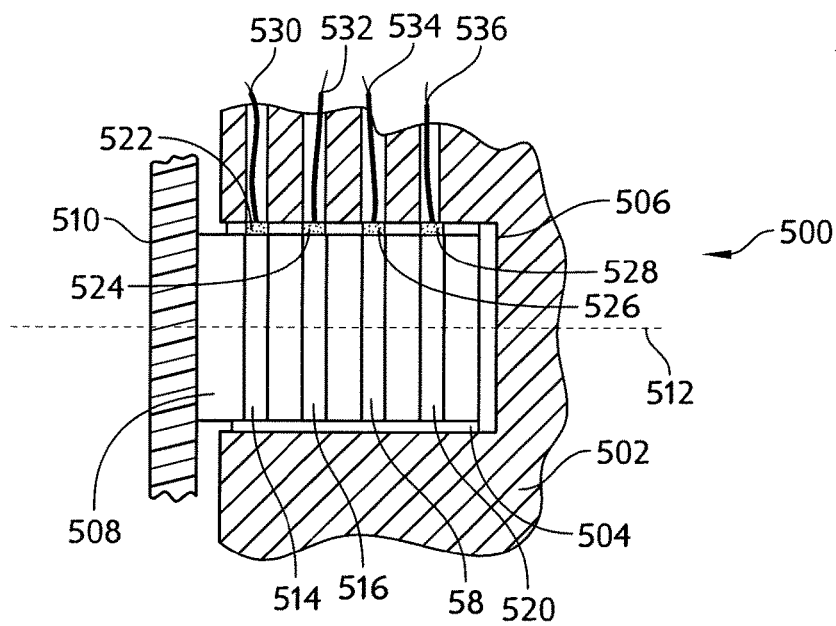
FIG. 16 is a cross-sectional view of an alternative embodiment of a side rail having a user interfaces pivotable relative to the side rail body, the user interface supported on a pivot that includes a number of conductors that engage brushes supported on the side rail body to maintain electrical connection therebetween.

In yet another embodiment shown in FIG. 16, a side rail 500 includes a side rail body 502 that is formed to include a journal cylinder 504 positioned in a cavity 506 in the body 502. A pivot 508 is coupled to a user interface 510 and supported in the journal 504 for rotation about an axis 512. The pivot 508 is formed to include four annular rings 514, 516, 518, and 520. Each of the annular rings 514, 516, 518, and 520 is a conductor that is operatively coupled to an independent wire (not shown) associated with each of the annular rings 514, 516, 518, and 520 and connected to circuitry in the user interface 510. Each of the annular rings 514, 516, 518, and 520 engages a respective brush 522, 524, 526, 528. Each brush 522, 524, 526, and 528 is electrical to vacation with a respective conductor 530, 532, 534, and 536. Conductor 530 is a power line, conductor 532 is a ground line, conductor 534 is a first member of a twisted-pair used for serial communications and conductor 536 is the second conductor of the twisted-pair.

In the embodiment of FIG. 16, there is no wireless transfer of power or data between the side rail body 502 and user interface 510, but communication occurs through the physical connection between the brushes 522, 524, 526, and 528 and the respective annular rings 514, 516, 518, and 520. In the embodiment of FIG. 16, the weight of the user interface 510 below the axis 512 causes the pivot 508 to rotate in the journal 504 for as the side rail 500 moves with a head section 450. Thus, the user interface 510 maintains a generally vertical orientation similar to that of the user interface 452 discussed above throughout the range of motion of the side rail 500.

Figure 17:
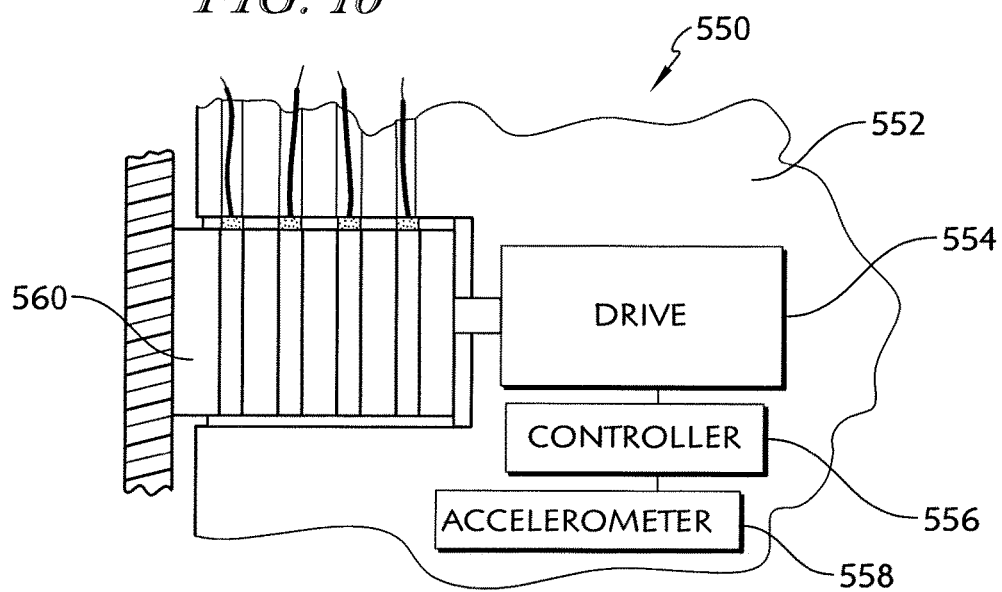
FIG. 17 is a cross-sectional view of yet another embodiment of the side rail having a user interface pivotable relative to the side rail body, the user interface supported on a pivot that is rotated by a drive control by controller that is responsive to the position of the side rail based upon information provided by an accelerometer.

In another embodiment shown in FIG. 17, a side rail 550 includes a side rail body 552 which supports a drive 554 controlled by controller 556. The controller 556 is operable to receive the signal from an accelerometer 558 which is indicative of the elevation of the side rail 550. The drive 554 is controlled by the controller to rotate a pivot 560 which is similar to the pivot 508 of the illustrative embodiment of FIG. 16. The remaining structure of the side rail 550 has the same structure as the side rail 500 with the user interface being moved relative to the body 552 by the drive 554 as opposed to gravity as described in the description of side rail 500.

Figure 18:
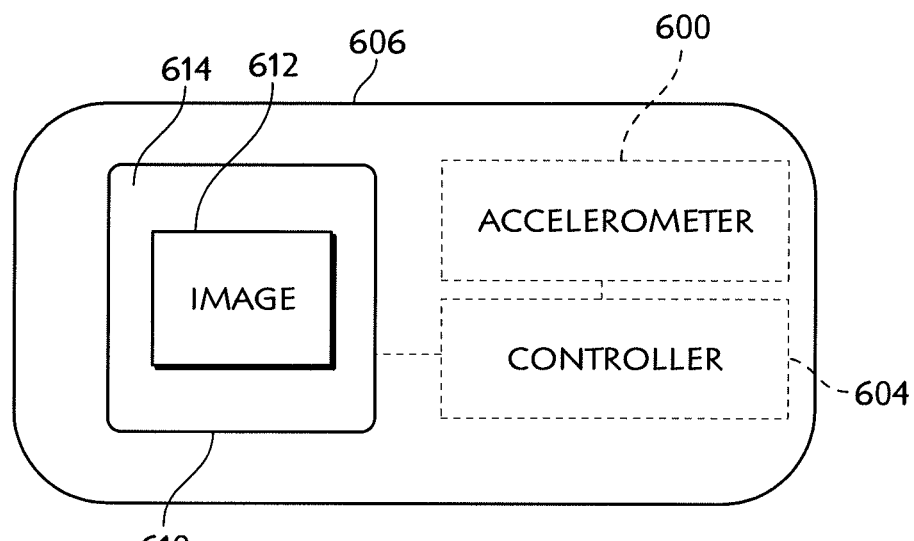
FIG. 18 is a diagram of a side rail having accelerometer in communication with a controller of the side rail that communicates the position of the side rail relative to gravity to user interface to control the orientation of the image on the user interface, the image in a first orientation.
Figure 19:
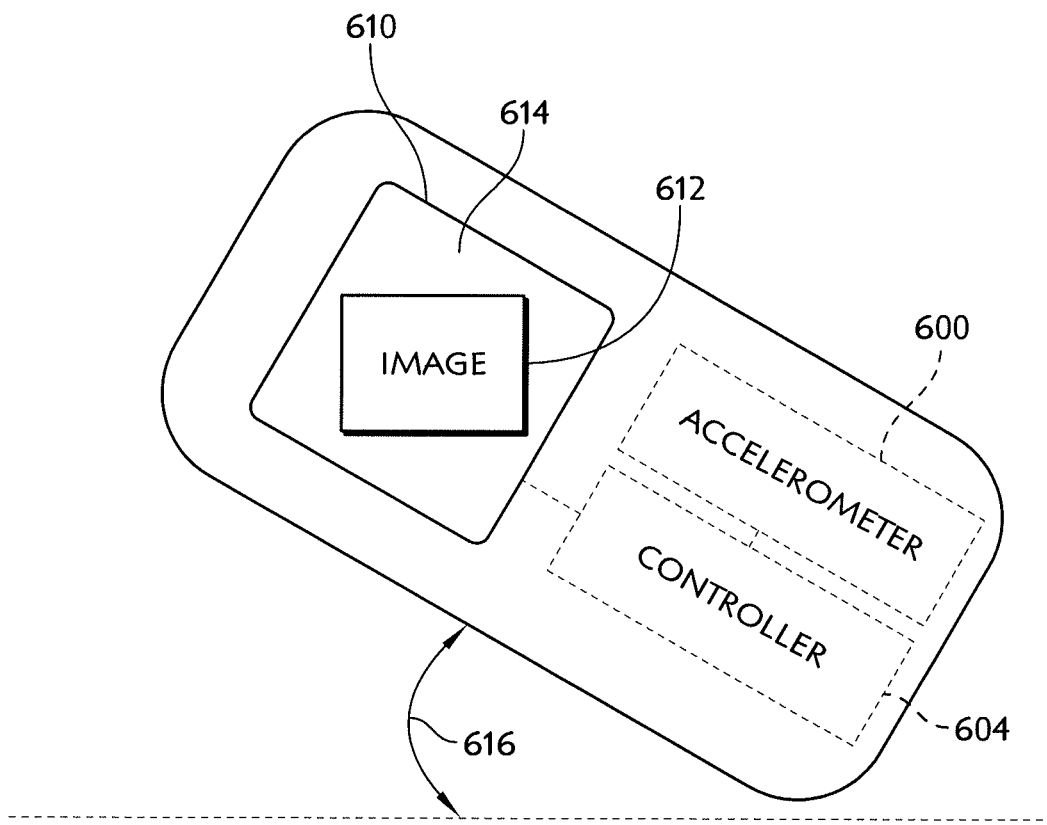
FIG. 19 is a plan view similar to FIG. 18 with the side rail in a second orientation and the image on the user interface being rotated to maintain the generally vertical orientation of the image.

Yet another embodiment shown in FIGS. 18 and 19, the accelerometer 600 may provide feedback to the controller 604 which then communicates with the user interface 610 to inform the user interface 610 of the angular orientation. The user interface 610 does not move physically relative to the side rail body 606, but software in the user interface 610 rotates the image 612 through an angle 616 and functionality of user-interface 610 so that the image 612 is maintained in a vertical orientation relative to horizontal, including user inputs that may be displayed on a touch screen 614 of the user interface 610. This has the benefit of eliminating the potential for failures at a mechanical interface when the user interface moves relative to a side rail body of described above.

It should be understood that each of the side rail embodiments 500 and 550 may wirelessly receive electrical signals in a manner similar to the side rail 448 of FIGS. 9-12 with the connections between the side rail body in user interface being the mechanical engagement of brushes 522, 524, 526, 528 with annular conductors 514, 516, 518, and 522 eliminate the wireless transmission at the user interface 510. Those of ordinary skill the art will also recognize that an electrical connection may be transferred through a linkage connecting the respective side rail 500 or 550 and the upper frame 444 as described, for example, in U.S. Pat. No. 7,073,220 entitled "BED SIDERAIL HAVING A LATCH" which is incorporated in it's entirety by reference herein. Functionality of the disclosed user interfaces such as user interfaces 452, 472, or 510 may include various functionality, such as the functionality disclosed in U.S. Patent Application Publication No. 2008/0235872 entitled "USER INTERFACE FOR HOSPITAL BED," which is incorporated in it's entirety by reference herein.

It should be understood that the disclosure herein includes variations which may be interchanged to arrive at embodiments that include portions of the different illustrative embodiments shown herein. For example, the embodiment of FIG. 1 which includes the receiver 12 mounted on the headboard 46 may be combined with the transmitter 418 mounted to the illustrative headboard 446 of FIG. 9. It should be understood that the present disclosure includes the ability to transfer power and/or data between environmental structures and portions of the patient support apparatus. In addition, the present disclosure contemplates that the use of wireless transmitters and receivers may permit the transfer of power and data between a first component and a second component which moves relative to the first component without the need for a physical connection between the two components, thereby eliminating the potential for failure of electrical conductors due to damage or fatigue the develops over multiple movements.

The benefit of using wireless couplers to transfer power and/or data between a first component and a second component that moves relative to the first component includes eliminating potential trip risks in excess cabling. It also includes the benefit of having reduced cabling between frames of the patient support apparatus. In addition, the potential for a user interface to be maintained in a particular orientation during movement of frame members of the patient support apparatus improves the usability of user interface for caregivers.

A similar benefit may be achieved when a computer cart 700 utilizes a wireless coupler 702 to wirelessly transfer power and/or data between a transmitter 704 positioned on the floor and a receiver 706 positioned in the cart 700. Carts, such as the illustrative cart 700, are used by caregivers and moved from room to room to perform data entry while the caregivers move between patients. The illustrative cart 700 includes a control system 708 which communicates with a computer 710. A user input device 712 such as a keyboard, for example, is supported on a frame member 714 of the cart 700. A display or monitor, 716 is also supported on the frame 714.

The receiver 706 communicates with the control system 708 which includes at least one battery (not shown) that powers the electrical systems of the cart 700 when the cart is not position with the receiver 706 adjacent the transmitter 704. The cart 700 includes casters 718 and 720 which supports a lower frame 722 and allows the cart 700 to be moved over the floor 48. The illustrative cart includes drawers 724 and 726 which provide for storage of medical supplies such as syringes, bandages, disposable thermometer sleeves, and the like as well as other equipment or supplies that may be required by the caregiver. When the cart 700 is positioned over the transmitter 704 in a docked position, power and/or data may be transferred between the transmitter 704 and receiver 706, with the data connection being a higher speed than a standard wireless Wi-Fi connection. The network 38 may also be in communication with the wireless coupler controller 34 as described above.

Figure 21:
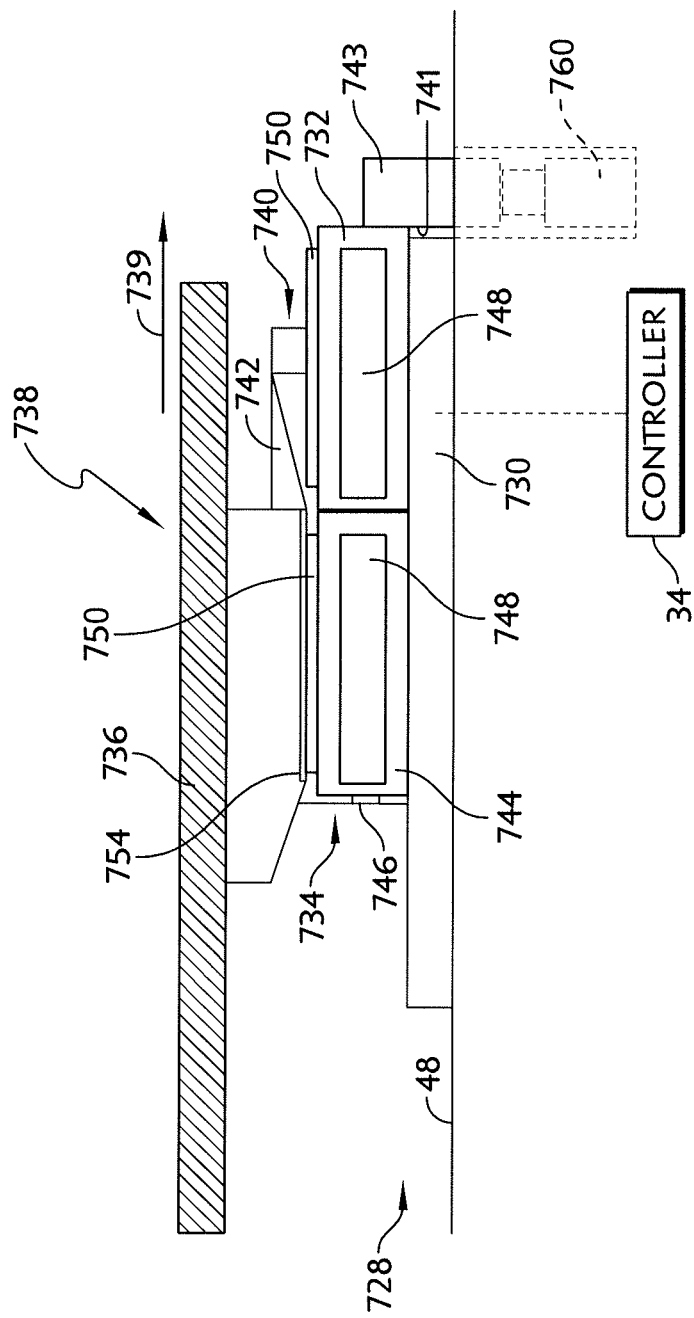
FIG. 21 is a side view of a portion of a cart having a structure for hot swapping batteries positioned adjacent a hot swap station.
Figure 22:
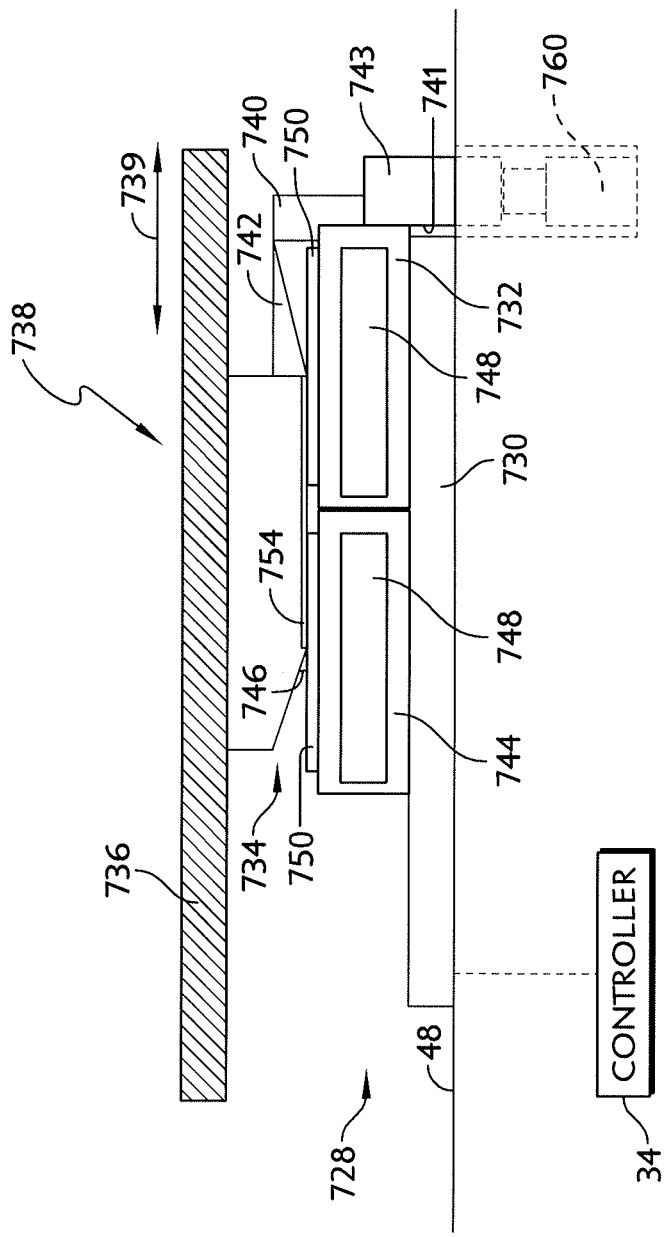
FIG. 22 is a side view similar to FIG. 21 with the cart position so that a first battery is engaging a battery grip while a second battery is simultaneously being ejected from the battery grip, the leads of both batteries simultaneously engaged to maintain power to the cart.
Figure 23:
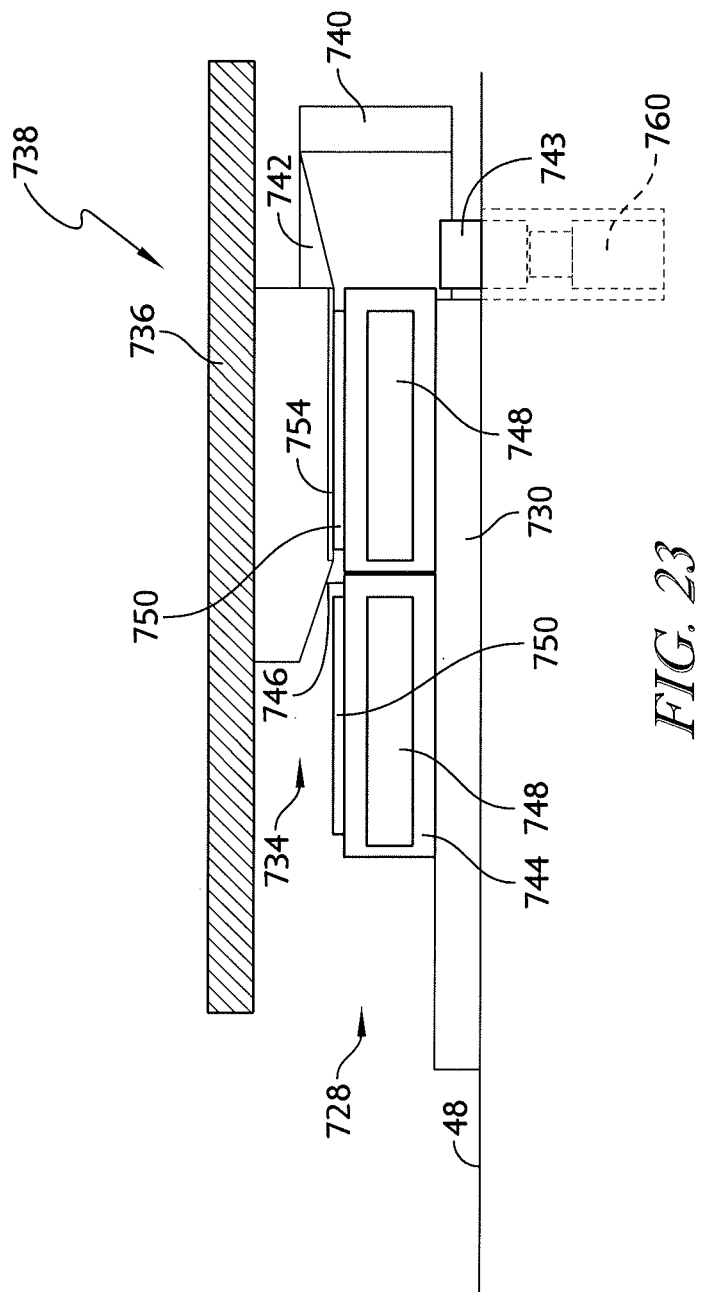
FIG. 23 is a side view similar to FIGS. 21-22, the hot swap complete as shown in FIG. 23.

In yet another embodiment, a hot-swap station 728 includes an inductive charging pad 730 that is positioned on the floor 48 so that a battery 732 may be positioned on the inductive charging pad 730, the inductive charging pad receiving power from a wireless coupler controller 34 as shown in FIG. 20. A frictional battery grip 734 positioned on the bottom of a frame 736 of a cart 738 includes guides 740 and 742 which engage the battery 732 as the cart is moved over the hot-swap station 728. The guides capture the battery 732 and as the cart is moved in the direction of arrow 739 the battery engages a surface 741 of a bumper 743 so that the battery 732 is pushed into the battery grip 734. The battery 732 displaces a battery 744 which is pushed out of a backside 746 of the battery grip 734. The battery 732 includes a negative contact 748 positioned on the side of the battery 732 and a positive contact 750 position on the top of the battery 732. As shown progressively in FIGS. 20-22, as battery 732 engages the grip 734, the negative contact 748 contacts a side 752 of the grip 734 and the positive contact 750 contacts a surface 754 of the grip 734. Thus, the battery 732 is actively engaged in transferring power to the cart 738 as it is being moved into the grip and displacing the battery 744. In this way, the batteries 732 and 744 are "hot swapped" without powering down the cart 738. Once the frame 736 of the cart 738 engages the bumper 743, the battery 744 is disengaged from the frictional grip 734 and rests on the inductive pad 730. The bumper can then be retracted into the floor 48 by an actuator 760 to permit cart to continue to move and leave the battery 744 on the inductive pad 730 to be charged.

Utilizing the hot swapping approach disclosed above a cart or a patient support apparatus may be continued to be powered while batteries are hot swapped eliminating the need for power cords and the requirement that the particular device such as a cart or a patient support apparatus be maintained in a particular position to receive a charge. This approach has the benefit of maintaining power to the device and quickly changing a battery without the need for a caregiver to handle the batteries, thereby reducing the opportunity for the transfer of contamination. When this approach is used, the device, such as a cart or patient support apparatus, for example, may maintain wireless communication utilizing traditional wireless technology as is known in the art. It should be understood that hot swapping may be used in conjunction with other embodiments disclosed herein that permit wireless transfer of power and/or data between moving members of a device.

Although certain illustrative embodiments have been described in detail above, variations and modifications exist within the scope and spirit of this disclosure as described and as defined in the following claims.

The invention claimed is:

1. A patient support apparatus comprising
a first member,
a second member movable relative to the first member, and
a first wireless coupler including a first portion positioned on the first member and a second portion positioned on the second member, the first wireless coupler operable to transfer electrical power from the first portion to the second portion throughout the range of motion of the second member as the second member moves between a first position and a second position relative to the first member,
wherein the second member comprises a side rail, and
wherein the patient support apparatus includes a first receiver operable to receive wireless power from an architectural structure spaced apart from the patient support apparatus, the power received by the first receiver being used to power components on the patient support apparatus in real time during operation of the patient support apparatus.

2. A patient support apparatus comprising
a first member,
a second member movable relative to the first member, and
a first wireless coupler including a first portion positioned on the first member and a second portion positioned on the second member, the first wireless coupler operable to transfer electrical power from the first portion to the second portion throughout the range of motion of the second member as the second member moves between a first position and a second position relative to the first member,
wherein the second member comprises a user interface and the first member comprises a side rail.

3. The patient support apparatus of claim 2, wherein the patient support apparatus further comprises a third member supported from the second member and movable relative to the second member, and a second wireless coupler operable to transfer electrical power from the second member to the third member throughout the range of motion of the third member as the third member moves between a first position and a second position relative to the second member.

4. The patient support apparatus of claim 3, wherein the first member includes a first receiver operable to receive wireless power from an architectural structure spaced apart from the patient support apparatus, the power received by the first receiver being used to power components on the third member in real time during operation of the patient support apparatus.

5. The patient support apparatus of claim 3, wherein the patient support apparatus includes a first receiver operable to receive wireless power from an architectural structure spaced apart from the patient support apparatus, the power received by the first receiver being used to power components on the patient support apparatus in real time during operation of the patient support apparatus.

6. The patient support apparatus of claim 2, wherein the patient support apparatus further comprises a frame supporting the side rail such that the side rail is movable relative to the frame, and the frame includes a wireless coupler operable to transfer electrical power from the frame to the side rail throughout the range of motion of the side rail as the side rail moves between a first position and a second position relative to the frame.

7. The patient support apparatus of claim 6, wherein the frame includes a first receiver operable to receive wireless power from an architectural structure spaced apart from the patient support apparatus, the power received by the first receiver being used to power components on the patient support apparatus in real time during operation of the patient support apparatus.

8. The patient support apparatus of claim 2, wherein the patient support apparatus includes a first receiver operable to receive wireless power from an architectural structure spaced apart from the patient support apparatus, the power received by the first receiver being used to power components on the patient support apparatus in real time during operation of the patient support apparatus.

9. A patient support apparatus comprising
a barrier, and
a user interface supported from the barrier, the user interface responsive to movement of the barrier relative to gravity to maintain the user interface in a first orientation throughout the range of movement of the barrier,
wherein the barrier further includes a plurality of brushes, and each brush includes an annular conductor forming a first electrical circuit that is maintained throughout the range of motion of the user interface relative to the barrier.

10. The patient support apparatus of claim 9, wherein gravity acts on the user interface to maintain user interface in the first orientation.

11. The patient support apparatus of claim 10, wherein the patient support apparatus includes a first receiver operable to receive wireless power from an architectural structure spaced apart from the patient support apparatus, the power received by the first receiver being used to power components on the patient support apparatus in real time during operation of the patient support apparatus.

12. The patient support apparatus of claim 9, further comprising a motor positioned on the barrier and engaged with user interface, the motor operable to move the user interface during movement of the barrier to maintain the user interface in the first orientation.

13. The patient support apparatus of claim 12, further comprising a controller coupled to the motor and an accelerometer coupled to the controller, the accelerometer providing a signal indicative of the orientation of the barrier, the controller modifying the position of the user interface relative to the barrier by operating the motor to maintain the user interface in the first orientation regardless of the position of the barrier.

14. The patient support apparatus of claim 13, wherein user interface includes a pivot received in a journal on a body of the barrier, the pivot movable within the journal to permit movement between the user interface and the barrier.

15. The patient support apparatus of claim 12, wherein the patient support apparatus includes a first receiver operable to receive wireless power from an architectural structure spaced apart from the patient support apparatus, the power received by the first receiver being used to power components on the patient support apparatus in real time during operation of the patient support apparatus.

16. The patient support apparatus of claim 9, wherein each brush is positioned to engage one of the conductors of the pivot.

17. The patient support apparatus of claim 9, wherein the patient support apparatus further comprises a frame supporting the barrier such that the barrier is movable relative to the frame, and the frame includes a wireless coupler operable to transfer electrical power from the frame to the barrier throughout the range of motion of the barrier as the barrier moves between a first position and a second position relative to the frame.

18. The patient support apparatus of claim 17, wherein the frame includes a first receiver operable to receive wireless power from an architectural structure spaced apart from the patient support apparatus, the power received by the first receiver being used to power components on the patient support apparatus in real time during operation of the patient support apparatus.

* * * * *